United States Patent [19]

Tsujihara et al.

[11] Patent Number: 5,830,873
[45] Date of Patent: Nov. 3, 1998

[54] PROPIOPHENONE DERIVATIVE AND A PROCESS FOR PREPARING THE SAME

[75] Inventors: Kenji Tsujihara, Urawa; Mitsuya Hongu, Omiya; Nobuyuki Funami, Tokyo-to; Masanori Inamasu, Misato; Kenji Arakawa, Urawa, all of Japan

[73] Assignee: Tanabe Seiyaku Co., Ltd., Osaka, Japan

[21] Appl. No.: 429,567

[22] Filed: Apr. 27, 1995

[30] Foreign Application Priority Data

May 11, 1994 [JP] Japan ................................... 6-096805
Nov. 17, 1994 [JP] Japan ................................... 6-282344

[51] Int. Cl.⁶ .......................... A61K 31/70; C07M 15/00
[52] U.S. Cl. .............................. 514/25; 536/4.1; 536/18.1
[58] Field of Search .................... 536/4.1, 18.1; 574/25

[56] References Cited

U.S. PATENT DOCUMENTS

| | | | |
|---|---|---|---|
| 3,984,394 | 10/1976 | Westall et al. | 514/8 |
| 4,031,260 | 6/1977 | Westall et al. | 426/548 |
| 4,049,715 | 9/1977 | Bell | 536/31 |
| 4,665,058 | 5/1987 | Diedrich et al. | 514/25 |
| 4,684,627 | 8/1987 | LeVeen et al. | 514/25 |
| 4,760,135 | 7/1988 | Diedrich et al. | 536/17.9 |
| 4,840,939 | 6/1989 | LeVeen et al. | 514/25 |
| 5,110,801 | 5/1992 | Leveen et al. | 514/34 |
| 5,424,406 | 6/1995 | Tsujihara et al. | 536/4.1 |

FOREIGN PATENT DOCUMENTS 0598359   5/1994   European Pat. Off. .

OTHER PUBLICATIONS

Diedrich, Biochim. Biophys. Acta, 71, 688 (1963).
Rossetti et al., Diabetes Care, 13, 610 (1990).
Rossetti et al., J. Clin. Invest., 79, 1510 (1987).
Rossetti et al., J. Clin. Invest., 80, 1037 (1987).
Kahn et al., J. Clin. Invest., 87, 561 (1991).
Unger et al., Diabetologia, 28, 119 (1985).
Oldendorf et al., Stroke, 14, 388 (1983).
Winget et al., Biochemistry, 8, 2067 (1967).
Vick et al., Amer. J. Physiol., 224, 552 (1973).
Diedrich, Arch. Biochem. Biophys., 117, 248 (1966).
Evans et al., Arch. Biochem. Biophys., 199, 342 (1980).
Bode et al., Biochim. Biophys. Acta, 290, 134 (1972).
Okada et al., Abstract of J. Nutr. Sci. Vitaminol.
T. Fujiwara et al., Diabetes, 37, 1549 (1988).
Szabo et al., Acta Aliment, 11, 31–37 (1982).

*Primary Examiner*—Elli Peselev
*Attorney, Agent, or Firm*—Birch, Stewart, Kolasch & Birch, LLP

[57] ABSTRACT

A propiophenone derivative of the formula [I]:

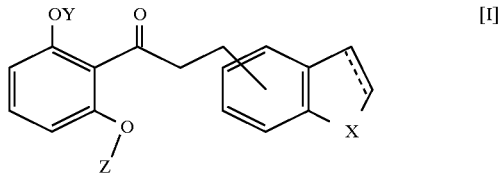

wherein X is O, S or methylene, OY is a protected or unprotected OH, Z is β-D-glucopyranosyl or 4-O-(α-D-glucopyranosyl)-β-D-glucopyranosyl or wherein one or more hydroxy groups of these groups may optionally be acylated, and the dotted line means the presence or absence of a double bond, or a pharmaceutically acceptable salt thereof. Said compounds have excellent hypoglycemic activity so that they are useful in the prophylaxis or treatment of diabetes.

18 Claims, No Drawings

PROPIOPHENONE DERIVATIVE AND A PROCESS FOR PREPARING THE SAME

TECHNICAL FIELD

The present invention relates to a novel propiophenone derivative having a hypoglycemic activity, and a process for preparing the same.

PRIOR ART

Although diet therapy is essential in the treatment of diabetes, when diet therapy does not sufficiently control the conditions of patients, insulin or an oral antidiabetic is additionally used. There have been used as antidiabetic biguanide compounds and sulfonylurea compounds, however, these antidiabetics have various side effects, for example, biguanide compounds cause lactic acidosis, and sulfonylurea compounds cause significant hypoglycemia. Under such circumstances, it has been desired to develop novel drugs for treatment of diabetes having no such side effects.

Recently, it has been reported that hyperglycemia participates in the outbreak and progressive impairment, i.e. glucose toxicity theory. That is, chronic hyperglycemia leads to decrease insulin secretion and contributes to increase insulin resistance, and as a result, the blood glucose concentration is increased so that diabetes is self-exacerbated [cf. Diabetologia, Vol. 28, p. 119 (1985); Diabetes Care, Vol. 13, p. 610 (1990), etc.]. Thus, by treating hyperglycemia, the aforementioned self-exacerbating cycle is interrupted so that the prophylaxis or treatment of diabetes is made possible.

As one of the methods for treating hyperglycemia, it is considered to excrete an excess amount of glucose directly into urine so that the blood glucose concentration is normalized.

Phlorizin is a glycoside which exists in barks and stems of Rosaceae (e.g. apple, pear, etc.). Recently, it has been found that phlorizin is an inhibitor of $Na^+$-glucose co-transporter which exists only at chorionic membrane of the intestine and the kidney, by which phlorizin inhibits the renal tubular glucose reabsorption and promotes the excretion of glucose so that the blood glucose is controlled. Based on this action of phlorizin, when the blood glucose concentration in diabetic animals is controlled at a normal level for a long time by subcutaneous daily administration of phlorizin but without using insulin, the conditions of diabetic animals are ameliorated to be normal [cf. Journal of Clinical Investigation, Vol. 79, p. 1510 (1987), Vol. 80, p. 1037 (1987), Vol. 87, p. 561 (1991), etc.].

However, when phlorizin is administered orally, most of it is hydrolyzed into glucose and phloretin, which is the aglycon of phlorizin, and hence, the amount of phlorizin to be absorbed is so little that the urine glucose excretion effect of phlorizin is very weak. Besides, phloretin, which is the aglycon of phlorizin, has been known to inhibit strongly a facilitated diffusion-type glucose transporter. So, when phloretin is intravenously administered to rats, the glucose concentration in brain of rats is decreased [cf. Stroke, Vol. 14, p. 388 (1983)]. Thus, when phlorizin is administered for a long time, there may be bad effects on various tissues, and hence, phlorizin has not been used as an antidiabetic.

BRIEF DESCRIPTION OF INVENTION

An object of the present invention is to provide a novel propiophenone derivative which inhibits the renal tubular glucose reabsorption by which it shows an urine glucose increasing activity, and shows an excellent hypoglycemic activity, and further an aglycon thereof has a weak inhibitory activity of facilitated diffusion-type glucose transporter. Another object of the present invention is to provide a hypoglycemic agent comprising as an active ingredient a propiophenone derivative of the present invention or a pharmaceutically acceptable salt thereof. A further object of the present invention is to provide a process for preparing a propiophenone derivative of the present invention.

DETAILED DESCRIPTION OF INVENTION

The present invention relates to a propiophenone derivative of the formula [I]:

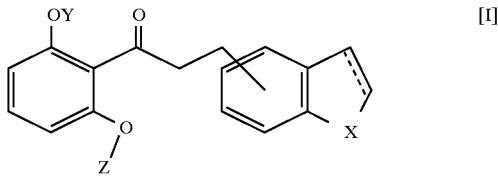

wherein X is an oxygen atom, a sulfur atom or a methylene group, OY is a protected or unprotected hydroxy group, Z is a β-D-glucopyranosyl group or 4-O-(α-D-glucopyranosyl)-β-D-glucopyranosyl group wherein one or more hydroxy groups of these groups may optionally be acylated, and the doffed line means the presence or absence of a double bond, or a pharmaceutically acceptable salt thereof.

In the present compounds [I], when OY is a protected hydroxy group, the protecting group may be any one which can be a protecting group for phenolic hydroxy group, for example, a lower alkoxy-lower alkyl group such as methoxymethyl group; an acyl group such as a lower alkanoyl group, a lower alkoxy-lower alkanoyl group, a lower alkoxycarbonyl group, benzoyl group; benzyl group, and the like.

In the present compounds [I], it is preferable to link the propiophenone moiety with a benzofuran, inden, benzothiophene ring, or dihydrated one of these groups (hereinafter these groups being referred to as "benzofuran ring, etc.") between the carbon atom at 3-position of the propiophenone moiety and the carbon atom at 5- or 6-position of the "benzofuran ring, etc.", especially at 5-position of the "benzofuran ring, etc.".

In the present compounds [I], when Z is a β-D-glucopyranosyl group or 4-O-(α-D-glucopyranosyl)-β-D-glucopyranosyl group wherein one or more hydroxy groups of these groups is/are acylated, the acyl group is, for example, a $C_{2-20}$ alkanoyl group, a lower alkoxy-lower alkanoyl group, a lower alkoxycarbonyl group, a benzoyl group or an amino acid residue which is obtained by removing a hydroxy group from the carboxyl group of a corresponding amino acid (wherein amino groups and/or carboxyl groups in said residue may be protected by a conventional protecting group).

The amino acid residue includes a group which is obtained by removing a hydroxy group from the carboxyl group of a natural amino acid such as glutamic acid, glutamine, serine, sarcosine, proline, phenylalanine, leucine, isoleucine, glycine, tryptophan, cysteine, histidine, tyrosine, or valine, or an antipode thereof, or a racemic compound thereof.

Suitable examples of the present propiophenone derivatives [I] are compounds of the formula [I] wherein Z is a β-D-glucopyranosyl group or 4-O-(α-D-glucopyranosyl)-β-D-glucopyranosyl group wherein one or more hydroxy groups of these groups may be acylated by a group selected from a $C_{2-20}$ alkanoyl group, a lower alkoxy-lower alkanoyl group, a lower alkoxy-carbonyl group and a benzoyl group.

The preferable compounds of the present invention are compounds of the formula [I] wherein OY is a lower alkanoyloxy group or a hydroxy group, Z is a β-D-glucopyranosyl group wherein the 2- and 3-hydroxy groups or the 6-hydroxy group are/is acylated by a group selected from a $C_{2-20}$ alkanoyl group, a lower alkoxy-lower alkanoyl group, a lower alkoxycarbonyl group and a benzoyl group, and the dotted line means the presence of a double bond, and among these compounds, those in which X is an oxygen atom or a sulfur atom, and OY is a hydroxy group are more preferable.

The pharmaceutically preferable compounds of the present invention are compounds of the formula [I] wherein X is an oxygen atom or a sulfur atom, OY is a hydroxy group, and Z is a β-D-glucopyranosyl group or a 4-O-(α-D-glucopyranosyl)-β-D-glucopyranosyl group.

The other pharmaceutically preferable compounds of the present invention are compounds of the formula [I] wherein X is an oxygen atom, OY is a lower alkanoyloxy group or a hydroxy group, Z is a 2,3-di-O-(lower alkanoyl)-β-D-glucopyranosyl group, a 2,3-di-O-(lower alkoxy-lower alkanoyl)-β-D-glucopyranosyl group, a 6-O-($C_{2-20}$-alkanoyl)-β-D-glucopyranosyl group, a 6-O-(lower alkoxy-lower alkanoyl)-β-D-glucopyranosyl group or a 6-O-benzoyl-β-D-glucopyranosyl group.

The pharmaceutically more preferable compounds of the present invention are compounds of the formula [I] wherein X is an oxygen atom, OY is a lower alkanoyloxy group or a hydroxy group, Z is a 2,3-di-O-(lower alkanoyl)-β-D-glucopyranosyl group, and especially 2'-[2,3-di-O-(lower alkanoyl)-β-D-glucopyranosyloxy]-6'-hydroxy-3-(5-benzo[b]furanyl)propiophenone and 2'-[2,3-di-O-(lower alkanoyl)-β-D-glucopyranosyloxy]-6'-(lower alkanoyloxy)-3-(5-benzo[b]furanyl)propiophenone are most preferable.

The propiophenone derivatives [I] of the present invention may be used in clinical use either in the free form or in the form of a pharmaceutically acceptable salt thereof. The pharmaceutically acceptable salt may be an alkali metal salt, etc.

The compounds [I] of the present invention or a pharmaceutically acceptable salt thereof may be administered either orally or parenterally, or in the form of a pharmaceutical preparation in admixture with a pharmaceutically acceptable carrier or diluent suitable for oral administration or parenteral administration. The pharmaceutically acceptable carrier or diluent may be, for example, binders (e.g. syrup, gum arabic, gelatin, sorbitol, tragacanth, polyvinylpyrrolidone, etc.), vehicles (e.g. lactose, sucrose, corn starch, potassium phosphate, sorbitol, glycine, etc.), lubricants (e.g. magnesium stearate, talc, polyethylene glycol, silica, etc.), disintegrators (e.g. potato starch, etc.), wetting agents (e.g. sodium laurylsulfate, etc.), and the like. These pharmaceutical preparations may be in the form of a solid preparation such as tablets, capsules, powders, granules, etc. or in the form of a liquid preparation such as solution, suspension, emulsion, etc, when administered orally. When administered parenterally, the pharmaceutical preparations may be in the form of an injection preparations or an intravenous drip preparation using distilled water for injection, an isotonic sodium chloride solution, an aqueous glucose solution, etc.

The dosage of the present compound [I] varies according to ages, weights and conditions of patients, or severity of diseases to be cured, but it is usually in the range of 0.1 to 100 mg/kg/day, preferably in the range of 1 to 40 mg/kg/day in case of oral administration. In case of parenteral administration, the dosage of the present compound [I] is in the range of 0.01 to 50 mg/kg/day, preferably in the range of 0.1 to 10 mg/kg/day.

The desired compound [I] of the present invention or a pharmaceutically acceptable salt thereof may be prepared by subjecting an acrylophenone compound of the formula [II]:

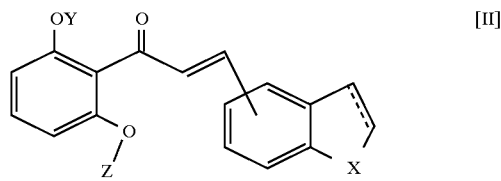

wherein X, OY, Z and the dotted line are the same as defined above, to reduction, and if necessary, followed by converting the product into a pharmaceutically acceptable salt thereof.

The reduction reaction is carried out by a conventional method, for example, by reduction with a metal hydride, catalytic reduction, etc. For example, the reduction with a metal hydride is carried out by using a metal hydride in a solvent, and the catalytic reduction is carried out by using a catalyst under atmospheric pressure of hydrogen gas in a solvent.

In the catalytic reduction, the catalyst may be any conventional one, but preferably palladium-carbon, platinum-carbon, platinum oxide, etc.

In the reduction with a metal hydride, the metal hydride may be any one which can reduce a double bond, but preferably ones which do not reduce a ketone, for example, sodium tellurium hydride (NaTeH), which is prepared according to a method disclosed in Synthesis, p. 545 (1978). Sodium tellurium hydride is usually used in an amount of 1 to 3 mole equivalents, preferably in an amount of 1 to 1.5 mole equivalent, to 1 mole equivalent of the compound [II].

The solvent may be any one which does not affect the reaction, for example, an organic solvent (e.g. methanol, ethanol, tetrahydrofuran, ethyl acetate, acetic acid, etc.), or a mixture of these organic solvents and water.

The reaction is carried out at a temperature of from under cooling to with heating, especially at a temperature from 10° C. to 30° C.

When the dotted line of the starting compound [II] means the presence of a double bond, said double bond may also be reduced by the reduction reaction, and the present invention also includes the compound thus obtained as well.

Besides, the compounds of the present invention thus obtained may be converted into another compound of the present invention as follows.

Among the present compounds [I], the compound of the formula [I] wherein Z is a β-D-glucopyranosyl group wherein the 6-hydroxy group is acylated, i.e. a compound of the formula [I-b]:

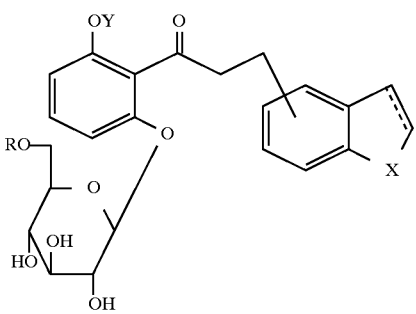

wherein R is an acyl group, and the other symbols are the same as defined above, may be prepared by subjecting the compound of the formula [I] wherein Z is a β-D-glucopyranosyl group, i.e. a compound of the formula [I-a]:

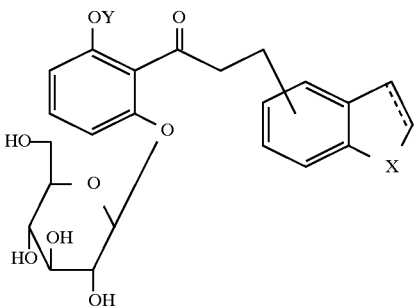

wherein the symbols are the same as defined above, to acylation.

Among the compounds [I] of the present invention, the compound of the formula [I] wherein Z is a β-D-glucopyranosyl group wherein the 2- and 3-hydroxy groups are acylated, i.e. a compound of the formula [I-c]:

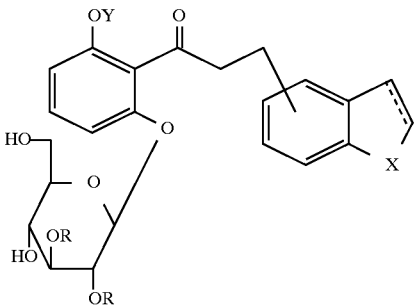

wherein the symbols are the same as defined above, may be prepared by protecting the 4- and 6-hydroxy groups of the β-D-glucopyranosyl group of the compound [I-a] to give a compound of the formula [III]:

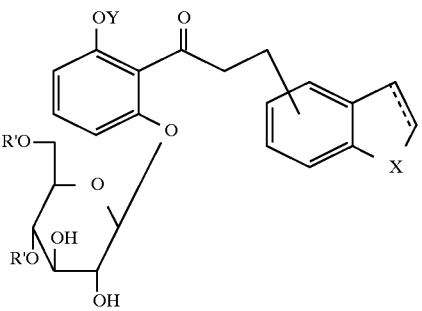

wherein R' is a protecting group, and the other symbols are the same as defined above, acylating the 2- and 3-hydroxy groups of the β-D-glucopyranosyl group of the compound [III], followed by removing said protecting groups therefrom.

In the compound [III], the protecting group may be any conventional protecting group, but these two protecting groups preferably combine each other to form a benzylidene group or an alkylidene group such as isopropylidene group.

The acylation reaction of the starting compound [I-a] or the compound [III] may be carried out by reacting an organic acid corresponding to the desired acyl group (e.g. $C_{1-19}$ alkylcarboxylic acid, a lower alkoxy-lower alkylcarboxylic acid, a lower alkoxycarboxylic acid, benzoic acid, etc.), or a salt thereof, or a reactive derivative thereof (hereafter these groups being referred to as acylating agent), with a starting compound.

The reaction of the organic acid corresponding to the desired acyl group, or a salt thereof with the starting compound is carried out in the presence or absence of a condensing agent in a suitable solvent, and the reaction of a reactive derivative of the organic acid corresponding to the desired acyl group with the starting compound is carried out in the presence or absence of an acid acceptor in a suitable solvent or without a solvent.

The salt of an organic acid may be, for example, an alkali metal salt or alkaline earth metal slat such as sodium salt, potassium salt, calcium salt, etc. When a salt of the organic acid is used in the condensation reaction, it is preferably used after converting it into a free acid thereof.

The reactive derivative of the organic acid includes, for example, an acid halide, an acid anhydride or an active ester of the corresponding organic acids.

The condensing agent may be any conventional one, for example, dicyclohexylcarbodiimide, diethyl cyanophosphate, carbonyldiimidazole, N,N-bis(2-oxo-3-oxazolidinyl)phosphinic chloride, etc.

The acid acceptor may be any conventional acid acceptors, for example, an inorganic base such as an alkali metal hydroxide (e.g. sodium hydroxide, potassium hydroxide); an alkali metal carbonate (e.g. sodium carbonate, potassium carbonate); an alkali metal hydrogen carbonate (e.g. sodium hydrogen carbonate, potassium hydrogen carbonate); an alkali metal hydride (e.g. sodium hydride, potassium hydride), or an organic base such as a tri-lower alkylamine (e.g. triethylamine, diisopropylethylamine); pyridine; dimethylaminopyridine; aniline; dimethylaniline, etc.

The solvent may be any conventional one which does not affect the reaction, for example, dichloromethane, dimethylformamide, tetrahydrofuran, acetonitrile, pyridine, etc.

The reaction is carried out at a temperature of from under cooling to with heating, preferably at a temperature from −10° C. to 100° C., more preferably at a temperature from 0° C. to 50° C.

In the acylation reaction, when OY of the starting compound is a free hydroxy group, said hydroxy group may occasionally be acylated, but the present invention also includes this compound thus obtained as well.

The compound [I-a] of the present invention is also useful as a synthetic intermediate of the present propiophenone derivatives [I] wherein Z is a β-D-glucopyranosyl group or 4-O-(α-D-glucopyranosyl)-β-D-glucopyranosyl group wherein one or more hydroxy groups of these groups is/are acylated.

Moreover, among the present compounds [I], the compound of the formula [I] wherein X is a methylene group and the dotted line means the presence of a double bond, i.e. an indene-type compound of the formula [I-d]:

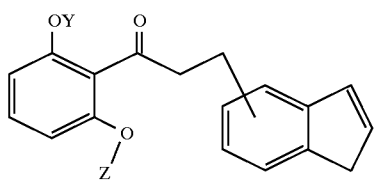

wherein the symbols are the same as defined above, may be prepared by removing a hydrogen atom and a leaving group: A from an indane-type compound of the formula [IV]:

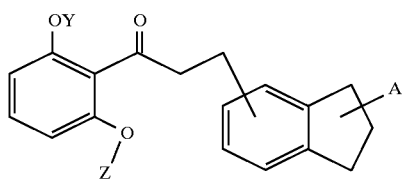

wherein A is a leaving group, and the other symbols are the same as defined above, which is prepared by previously introducing a leaving group: A into a compound of the formula [I] wherein X is a methylene group and the dotted line means the absence of a double bond.

The removal is carried out in the presence or absence of a base in a solvent or without a solvent.

The leaving group: A may be any conventional leaving group, preferably a halogen atom such as chlorine, bromine, etc., methanesulfonyloxy group, p-toluenesulfonyloxy group, and the like.

The base includes, for example, an organic base such as a tri-lower alkylamine (e.g. triethylamine, diisopropylethylamine, etc.); pyridine; dimethylaminopyridine; aniline; dimethylaniline; etc.

The solvent may be any conventional one which does not affect the reaction, for example, dichloromethane, dimethylformamide, tetrahydrofuran, pyridine, etc.

The reaction is carried out at a temperature of from under cooling to with heating, preferably with heating, more preferably at a temperature from 100° C. to 150° C.

By this removal, there may be obtained a mixture of a 5-indene-type compound and a 6-indene-type compound, and the present invention also includes this mixture as well. When a mixture of a 5-indene-type compound and a 6-indene-type compound is obtained, if necessary, both indene-type compounds are separated by chromatography, etc.

The starting compound [II] may be prepared by condensing an acetophenone compound of the formula [V]:

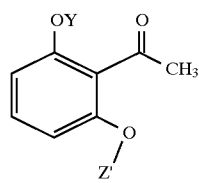

wherein Z' is a β-D-glucopyranosyl group or 4-O-(α-D-glucopyranosyl)-β-D-glucopyranosyl group wherein a hydroxy group of these groups may optionally be protected, and OY is the same as defined above, with an aldehyde derivative of the formula [VI]:

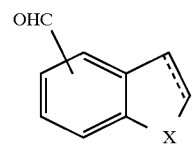

wherein the symbols are the same as defined above, and if necessary, removing the protecting group from the product, and further by acylating the product, if necessary.

When Z' of the starting compound [V] is a β-D-glucopyranosyl group having a protected hydroxy group or a 4-O-(α-D-glucopyranosyl)-β-D-glucopyranosyl group having a protected hydroxy group, the protecting group may be any conventional protecting group such as a lower alkanoyl group, and said protecting group may be removed by a conventional method such as hydrolysis.

The condensation reaction of the acetophenone compound [V] and the aldehyde derivative [VI] is carried out by a conventional method, for example, in the presence of a base (e.g. an alkali metal hydroxide, etc.) in a solvent (e.g. an organic solvent such as methanol, ethanol, or a mixture of these organic solvents and water) at a temperature of from under cooling to with heating, preferably at a temperature from 10° C. to 30° C.

When the acylation reaction is necessary in the preparation of the starting compound [II], the acylation reaction may be carried out by the same procedures as in the acylation reaction of the compound [I-a] or the compound [III]. The degree of the acylation, i.e. the acylation of all hydroxy groups or selective acylation of the specific hydroxy group of the glucosyl group, may be selected by controlling the difference of stereo-structural circumstance around the hydroxy groups, and/or the amount of the acylating agent.

The compound [II] thus obtained may be used in the subsequent reaction after purification, but may be used without purification.

The compound [IV] may be prepared by the processes as shown in the following scheme.

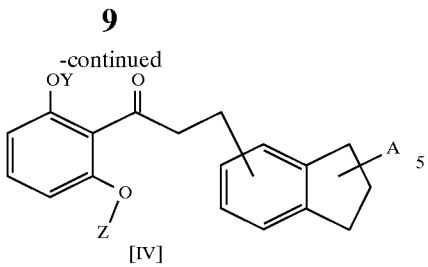

[IV]

wherein A' is a protected hydroxy group, and the other groups are the same as defined above, that is, by the steps:

a) preparing a Grignard reagent from the compound [VII] and magnesium by a conventional manner, reacting the reagent with dimethylformamide, etc. in a suitable solvent (e.g. tetrahydrofuran) to give a formylized compound [VIII], wherein a protecting group for A' may be any conventional protecting group which can be removed by a conventional method, for example, tetrahydropyranyl group;

b) condensing the compound [VIII] with the compound [V] to give the compound [IX], which is carried out by the same procedures as in the preparation of the compound [II];

c) reducing the compound [IX] to give the compound [X], which is carried out by the same procedures as in the preparation of the compound [I]; and d) removing the protecting group, converting the hydroxy group into a leaving group to give the compound [IV], wherein the conversion reaction of the hydroxy group into a leaving group is carried out by reacting with a halogenating agent, methanesulfonyl chloride, p-toluenesulfonyl chloride, etc. in a suitable solvent (e.g. pyridine) in the presence or absence of a base in a conventional manner.

The starting compound [V] of the present invention may be prepared (i) according to a method disclosed in Journal of Medicinal and Pharmaceutical Chemistry, vol. 5, p. 1054 (1962), for example, by reacting 2',6'-dihydroxyacetophenone with 2,3,4,6-tetra-O-acetyl-α-D-glucopyranosyl bromide in the presence of potassium hydroxide in an aqueous acetone, followed by protecting a phenolic hydroxy group, if necessary; or (ii) heating 2',6'-dihydroxyacetophenone with 2,3,4,6-tetra-O-acetyl-(α-D-glucopyranosyl bromide or 2,3,6-tri-O-acetyl-4-O-(2,3,4,6-tetra-O-acetyl-α-D-glucopyranosyl)-α-D-glucopyranosyl bromide in the presence of cadmium carbonate in toluene, refluxing the mixture, and if necessary, followed by protecting a phenolic hydroxy group.

In the present specification and claims, the lower alkoxy group means a straight chain or branched chain alkoxy group having 1 to 6 carbon atoms, preferably 1 to 4 carbon atoms, for example, methoxy group, ethoxy group, propoxy group, isopropoxy group, butoxy group, isobutoxy group, tertbutoxy group, etc.

The $C_{2-20}$ alkanoyl group means a straight chain or branched chain alkanoyl group having 2 to 20 carbon atoms, for example, acetyl group, propionyl group, butyryl group, 2-methylpropionyl group, valeryl group, pivaloyl group, lauryl group, myristoyl group, palmitoyl group, stearoyl group, etc.

Among the aforementioned alkanoyl groups, the lower alkanoyl group means a straight chain or branched chain alkanoyl group having 2 to 7 carbon atoms, preferably ones having 2 to 5 carbon atoms.

The β-D-glucopyranosyl has the structure of the following formula:

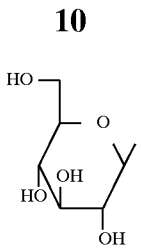

and the 4-O-(α-D-glucopyranosyl)-β-D-glucopyranosyl has the structure of the following formula:

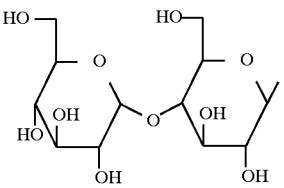

Effects

Experiment: Urine glucose increasing activity in rats

Method:

A test compound solution (dosage; 100 mg/kg) was orally administered twice at 8-hr intervals to male SD-rats (3 to 5 rats/group, 6 wk old). A test compound solution was prepared by adding Tween 80 (Nacalai Tesque, Ltd., Japan, final concentration: 0.5% aqueous solution) to a test compound (the compound of the following Examples or phlorizin) at a rate of 100 mg/5 ml. In the control group, a 0.5% aqueous Tween 80 solution (5 ml/kg) was administered instead of the test compound solution. Rats were housed individually into a metabolite cage, and urine was collected for 24 hours after the first administration of the test compound. After measuring the urine volume, the urine was centrifuged in order to remove the impurity, and the urine glucose concentration therein was determined by glucose-analyzer (Apec Co., Ltd.). The amount of the urine glucose (mg) excreted for 24 hours was determined based on the urine volume (ml), the urine glucose concentration therein (mg/dl), and the weights of rats, and expressed as mg/24 hr/200 g of body weight. The results are shown in Table 1.

TABLE 1

| In Tested Group (Example No.) | Urine glucose amount[*1] (mg/24 hr/200 g) |
| --- | --- |
| 1 | 591 ± 105 |
| 3 | 140 ± 10 |
| 4 | 461 ± 29 |
| 5[*2] | 326.7 ± 43.2 |
| 6 | 1281.9 ± 137.2 |
| 7 | 1198.8 ± 102.2 |
| 8 | 582.6 ± 18.0 |
| 9 | 719.9 ± 45.0 |
| 11 | 687.6 ± 47.7 |
| 13 | 727.7 ± 87.5 |
| 14 | 516.0 ± 9.4 |
| 15 | 235.8 ± 20.4 |
| 16 | 412.6 ± 33.1 |
| 17 | 331.3 ± 39.3 |
| Phlorizin | 12.7 ± 6.9 |
| Control group | 2.5 ± 1.3 |

[*1] Average ± standard deviation
[*2] A mixture was used as a test compound.

As is clear from the above results, the propiophenone derivative [I] of the present invention show about 11 to 100 times as strong urine glucose increasing activity as phlorizin does.

EXAMPLES

The present invention is illustrated in more detail by the following Examples and Reference Example, but should not be construed to be limited thereto.

Example 1

To a mixture of 2'-(2,3,4,6-tetra-O-acetyl-β-D-glucopyranosyloxy)-6'-hydroxyacetophenone (965 mg), benzo[b]furan-5-carbaldehyde (350 mg) and ethanol (10 ml) is added dropwise a 50% aqueous potassium hydroxide solution (2 ml), and the mixture is stirred at room temperature overnight. The mixture is evaporated to remove the solvent, and to the residue are added water and diisopropyl ether. The mixture is stirred, and the aqueous layer is collected. The aqueous layer is neutralized with a 10% hydrochloric acid under ice-cooling, and extracted with ethyl acetate. The resulting organic layer is washed with water, dried, and evaporated to remove the solvent to give crude 2'-(β-D-glucopyranosyloxy)-6'-hydroxy-3-(5-benzo[b]furanyl)acrylophenone. This product is added to a solution of sodium tellurium hydride in ethanol (15 ml), which is previously prepared from tellurium (383 mg) and sodium borohydride (270 mg), and the mixture is reacted at room temperature for 2.5 hours. The insoluble materials are removed by filtration, and to the filtrate are added water and ethyl acetate. The mixture is stirred, and the organic layer is collected, washed with water, dried, and evaporated to remove the solvent. The residue is purified by silica gel column chromatography to give 2'-(β-D-glucopyranosyloxy)-6'-hydroxy-3-(5-benzo[b]furanyl)propiophenone (480 mg).

NMR (DMSO-$d_6$) δ: 3.00 (2H, t, J=7.5 Hz), 3.1–3.4 (6H, m), 3.47 (1H, m), 3.71 (1H, ddd, J=1.7, 5.1, 11.4 Hz), 4.56 (1H, t, J=5.7 Hz), 4.93 (1H, d, J=7.4 Hz), 5.03 (1H, d, J=5.2 Hz), 5.10 (1H, d, J=4.6 Hz), 5.25 (1H, d, J=5.3 Hz), 6.55 (1H, d, J=8.2 Hz), 6.68 (1H, d, J=7.8 Hz), 6.87 (1H, dd, J=1.0, 3.2 Hz), 7.21 (1H, dd, J=1.8, 8.5 Hz), 7.24 (1H, t, J=8.3 Hz), 7.46 (1H, d, J=8.5 Hz), 7.53 (1H, d, J=1.3 Hz), 7.92 (1H, d, J=2.2 Hz), 10.98 (1H, s)

FABMS (m/z): 467 [(M+Na)$^+$]

Example 2

To a mixture of 2'-(2,3,4,6-tetra-O-acetyl-β-D-glucopyranosyloxy)-6'-hydroxyacetophenone (1500 mg), benzo[b]furan-5-carbaldehyde (545 mg) and ethanol (15 ml) is added dropwise a 50% aqueous potassium hydroxide solution (3 ml), and the mixture is stirred at room temperature overnight. The mixture is subjected to catalytic hydrogenation by using as a catalyst 10% platinum on activated carbon (303 mg) under atmospheric pressure. The catalyst is removed by filtration, and the filtrate is concentrated under reduced pressure. To the residue are added toluene and water, and the mixture is stirred. The aqueous layer is collected by filtration, acidified with a 10% hydrochloric acid under ice-cooling, and extracted with ethyl acetate. The obtained organic layer is washed with water, dried, and evaporated to remove the solvent. The residue is purified by silica gel column chromatography to give 2'-(β-D-glucopyranosyloxy)-6'-hydroxy-3-(5-benzo[b]furanyl)propiophenone (982 mg). The physical properties of this product are the same as those of the compound of Example 1.

Example 3

2'-(2,3,4,6-Tetra-O-acetyl-β-D-glucopyranosyloxy)-6'-hydroxyacetophenone (1268 mg) and benzo[b]furan-5-carbaldehyde (911 mg) are treated in the same manner as in Example 1 to give crude 2'-(β-D-glucopyranosyloxy)-6'-hydroxy-3-(5-benzo[b]furanyl)acrylophenone. This product is dissolved in a mixture of ethanol (20 ml) and acetic acid (2 ml), and the mixture is subjected to catalytic hydrogenation by using 10% palladium-carbon (0.5 g) under atmospheric pressure. The catalyst is removed by filtration, and the filtrate is concentrated under reduced pressure. To the residue are added ethyl acetate and water, and the mixture is stirred. The organic layer is collected, washed with a saturated aqueous sodium hydrogen carbonate solution, dried, and evaporated to remove the solvent. The residue is pulverized with chloroform-diisopropyl ether, and the obtained powder is collected by filtration and dried to give 2'-(β-D-glucopyranosyloxy)-6'-hydroxy-3-(2,3-dihydro-5-benzo[b]furanyl)propiophenone (920 mg).

NMR (DMSO-$d_6$) δ: 2.81 (2H, t, J=7.5 Hz), 3.12 (2H, t, J=8.6 Hz), 3.15–3.38 (6H, m), 3.46 (1H, m), 3.70 (1H, m), 4.46 (2H, t, J=8.7 Hz), 4.55 (1H, t, J=5.7 Hz), 4.91 (1H, d, J=7.5 Hz), 5.02 (1H, d, J=5.2 Hz), 5.09 (1H, d, J=4.7 Hz), 5.20 (1H, d, J=5.3 Hz), 6.55 (1H, d, J=8.3 Hz), 6.62 (1H, d, J=8.1 Hz), 6.67 (1H, d, J=7.7 Hz), 6.95 (1H, dd, J=1.8, 8.1 Hz), 7.11 (1H, broad-s), 7.24 (1H, t, J=8.3 Hz), 11.00 (1H, s)

FABMS (m/z): 469 [(M+Na)$^+$]

Example 4

The corresponding starting compounds are treated in the same manner as in Example 1 to give 2'-(β-D-glucopyranosyloxy)-6'-hydroxy-3-(5-benzo[b]thienyl)propiophenone.

NMR (DMSO-$d_6$) δ: 3.03 (2H, t, J=7.3 Hz), 3.1–3.4 (6H, m), 3.47 (1H, m), 3.71 (1H, ddd, J=1.5, 5.1, 11.7 Hz), 4.56 (1H, t, J=5.7 Hz), 4.93 (1H, d, J=7.3 Hz), 5.03 (1H, d, J=5.1 Hz), 5.10 (1H, d, J=4.4 Hz), 5.26 (1H, d, J=5.1 Hz), 6.55 (1H, d, J=8.1 Hz), 6.69 (1H, d, J=8.1 Hz), 7.26 (1H, t, J=8.1 Hz), 7.29 (1H, dd, J=1.5, 8.8 Hz), 7.38 (1H, dd, J=0.7, 5.5 Hz), 7.70 (1H, d, J=5.5 Hz), 7.76 (1H, d, J=0.7 Hz), 7.87 (1H, d, J=8.1 Hz), 11.01 (1H, s)

FABMS (m/z): 483 [(M+Na)$^+$]

Example 5

(1) 6-Bromoindan-1-ol (3.01 g) and dihydropyrane (1.78 g) are dissolved in dichloromethane (50 ml), and thereto is added pyridinium p-toluenesulfonate (178 mg), and the mixture is stirred at room temperature for 1.5 hour. The reaction solution is washed with a saturated aqueous sodium hydrogen carbonate solution, dried, and evaporated to remove the solvent. The residue is purified by silica gel column chromatography (solvent; hexane/ethyl acetate) to give 6-bromo-1-tetrahydropyranyloxyindane (4.10 g).

MS (m/z): 296, 298 (M$^+$)

(2) A mixture of magnesium (228 mg) and iodine (3 mg) in tetrahydrofuran (3 ml) is heated at 60° C. under argon atmosphere, and thereto is added dropwise with stirring a solution of 6-bromo-1-tetrahydropyranyloxyindane (2.60 g) in tetrahydrofuran (5 ml). After addition, the mixture is stirred at 70° C. for one hour. To the mixture is added dropwise a solution of dimethylformamide (959 mg) in tetrahydrofuran (2 ml) under ice-cooling, and the mixture is stirred under ice-cooling for one hour. The reaction solution is poured into a mixture of ice-acetic acid, and extracted with ethyl acetate. The extract is washed with water, dried, and evaporated to remove the solvent. The residue is purified by silica gel column chromatography (solvent; hexane/ethyl acetate) to give 1-tetrahydropyranyloxyindane-6-carbaldehyde (1081 mg).

MS (m/z): 246 (M⁺)

(3) 2'-(2,3,4,6-Tetra-O-acetyl-β-D-glucopyranosyloxy)-6'-hydroxyacetophenone and 1-tetrahydropyranyloxyindane-6-carbaldehyde are treated in the same manner as in Example 1 to give 2'-(β-D-glucopyranosyloxy)-6'-hydroxy-3-(1-tetrahydropyranyloxyindan-6-yl)propipheneone.

FABMS (m/z): 567 [(M+Na)⁺]

(4) 2'-(β-D-Glucopyranosyloxy)-6'-hydroxy-3-(1-tetrahydropyranyloxyindan-6-yl)propiophenone (1160 mg) is dissolved in pyridine (10 ml), and thereto is added acetic anhydride (1.63 g), and the mixture is stirred at room temperature overnight. The mixture is evaporated to remove the pyridine, and the residue is dissolved in ethyl acetate, washed with water, dried, and evaporated to remove the solvent to give 2'-(2,3,4,6-tetra-O-acetyl-β-D-glucopyranosyloxy)-6'-acetoxy-3-(1-tetrahydropyranyloxyindan-6-yl)propiophenone (1438 mg). This product is dissolved in a mixture of acetic acid (20 ml), tetrahydrofuran (10 ml) and water (5 ml), and the mixture is stirred. The organic layer is collected, washed with water, dried, and evaporated to remove the solvent. The residue is purified by silica gel column chromatography (solvent; chloroform/acetone) to give 2'-(2,3,4,6-tetra-O-acetyl-β-D-glucopyranosyloxy)-6'-acetoxy-3-(1-hydroxyindan-6-yl)propiophenone (1071 mg).

FABMS (m/z): 693 [(M+Na)⁺]

(5) 2'-(2,3,4,6-Tetra-O-acetyl-β-D-glucopyranosyloxy)-6'-acetoxy-3-(1-hydroxyindan-6-yl)propiophenone (1054 mg) is dissolved in pyridine (30 ml), and thereto is added p-toluene sulfonylchloride (329 mg), and the mixture is stirred at 75° C. overnight. To the mixture is added p-toluene sulfonylchloride (150 mg), and the mixture is refluxed for two days. The mixture is evaporated to remove the pyridine, and the residue is dissolved in ethyl acetate. The mixture is washed with water, dried, and evaporated to remove the solvent. The residue is purified by silica gel column chromatography (solvent; chloroform/ethyl acetate) to give a mixture of 2'-(2,3,4,6-tetra-O-acetyl-β-D-glucopyranosyloxy)-6'-hydroxy-3-(inden-6-yl)propiophenone and 2'-(2,3,4,6-tetra-O-acetyl-β-D-glucopyranosyloxy)-6'-hydroxy-3-(inden-5-yl)propiophenone (1:1) (676 mg).

FABMS (m/z): 633 [(M+Na)⁺]

(6) A mixture (660 mg) of 2'-(2,3,4,6-tetra-O-acetyl-β-D-glucopyranosyloxy)-6'-hydroxy-3-(inden-6-yl)propiophenone and 2'-(2,3,4,6-tetra-O-acetyl-β-D-glucopyranosyloxy)-6'-hydroxy-3-(inden-5-yl)propiophenone is dissolved in methanol (20 ml), and thereto are added potassium carbonate (1 g) and water (0.2 ml), and the mixture is stirred at room temperature for one hour. The reaction solution is neutralized with a 10% hydrochloric acid under ice-cooling, and thereto is added ethyl acetate. The mixture is stirred, and the organic layer is collected. The organic layer is washed with water, dried, and evaporated to remove the solvent. The residue is purified by silica gel column chromatography (solvent; chloroform/methanol) to give a mixture of 2'-(β-D-glucopyranosyloxy)-6'-hydroxy-3-(inden-6-yl)propiophenone and 2'-(β-D-glucopyranosyloxy)-6'-hydroxy-3-(inden-5-yl)propiophenone (1:1) (441 mg).

NMR (DMSO-d₆) δ: 2.94 (2Hx2, t, J=7.5 Hz), 3.1–3.4 (8Hx2, m), 3.46 (1Hx2, m), 3.70 (1Hx2, ddd, J=1.9, 5.3, 11.7 Hz), 4.55 (1Hx2, t, J=5.4 Hz), 4.93 (1Hx2, d, J=7.2 Hz), 5.02 (1Hx2, d, J=5.2 Hz), 5.09 (1Hx2, d, J=4.7 Hz), 5.22 (1Hx2, d, J=5.1 Hz), 6.53 (1H, dt, J=5.5, 2.0 Hz), 6.55 (1Hx2, d, J=8.4 Hz), 6.58 (1H, dt, J=5.5, 2.0 Hz), 6.68 (1Hx2, d, J=8.1 Hz), 6.88 (1Hx2, m), 7.07 (1H, dd, J=1.5, 7.6 Hz), 7.14 (1H, dd, J=1.5, 7.8 Hz), 7.25 (1Hx2, t, J=8.3 Hz), 7.29 (1H, d, J=8.0 Hz), 7.31 (1H, s), 7.36 (1H, d, J=7.6 Hz), 7.39 (1H, s), 11.02 (1Hx2, s)

FABMS (m/s): 465 [(M+Na)⁺]

Example 6

(1) To a mixture of 2'-(β-D-glucopyranosyloxy)-6'-hydroxy-3-(5-benzo[b]furanyl)propiophenone (4.4 g) and dichloromethane (80 ml) are added benzaldehyde dimethyl acetal (3.04 g) and p-toluenesulfonic acid (0.19 g), and the mixture is stirred at room temperature for two hours. The mixture is evaporated to remove the solvent, and the resulting residue is dissolved in ethyl acetate. The organic layer is washed with water, dried, and evaporated to remove the solvent. The residue is purified by silica gel column chromatography (solvent; chloroform/methanol) to give 2'-(4,6-O-benzylidene-β-D-glucopyranosyloxy)-6'-hydroxy-3-(5-benzo[b]furanyl)propiophenone (5.84 g).

NMR (DMSO-d₆) δ: 3.00 (2H, t, J=7.6 Hz), 3.2–3.4 (6H, m), 3.5–3.6 (1H, 15 m), 4.20 (1H, t, J=5.1 Hz), 5.17 (1H, d, J=7.7 Hz), 5.47 (1H, d, J=5.2 Hz), 5.58 (1H, s), 5.59 (1H, d, J=5.8 Hz), 6.57 (1H, d, J=8.1 Hz), 6.72 (1H, d, J=8.1 Hz), 6.89 (1H, dd, J=1.0, 2.2 Hz), 7.21 (1H, dd, J=1.9, 8.5 Hz), 7.25 (1H, t, J=8.3 Hz), 7.35–7.55 (7H, m), 7.94 (1H, d, J=2.2 Hz), 10.82 (1H, s)

FABMS (m/z): 555 [(M+Na)⁺]

(2) 2'-(4,6-O-Benzylidene-β-D-glucopyranosyloxy)-6'-hydroxy-3-(5-benzo[b]furanyl)propiophenone (5.78 g) is dissolved in pyridine (50 ml), and thereto is added acetic anhydride (6.65 g), and the mixture is stirred at room temperature for four hours. To the reaction solution is added ethyl acetate, and the mixture is poured into ice-1 0% hydrochloric acid. The mixture is stirred, and the organic layer is collected, washed with water, dried, and evaporated to remove the solvent to give crude 2'-(2,3-di-O-acetyl-4,6-O-benzylidene-β-D-glucopyranosyloxy)-6'-acetoxy-3-(5-benzo[b]furanyl)propiophenone (7.24 g). This product (520 mg) is dissolved in acetic acid (10 ml), and thereto are added water (1.5 ml) and p-toluenesulfonic acid (45 mg). The mixture is stirred at 50° C. for five hours, and thereto are added water and ethyl acetate. The mixture is stirred, and the organic layer is collected, washed with water, dried, and evaporated to remove the solvent. The residue is purified by silica gel column chromatography (solvent; chloroform/methanol) to give 2'-(2,3-di-O-acetyl-β-D-glucopyranosyloxy)-6'-acetoxy-3-(5-benzo[b]furanyl)propiophenone (360 mg).

NMR (DMSO-d₆) δ: 1.88 (3H, s), 2.00 (6H, s), 2.9–3.1 (4H, m), 3.5–3.8 (4H, m), 4.75 (1H, t, J=5.5 Hz), 4.90 (1H, dd, J=8.0, 9.8Hz), 5.11 (1H, t, J=9.2 Hz), 5.50 (1H, d, J=7.9 Hz), 5.59 (1H, d, J=5.7 Hz), 6.88 (1H, d, J=7.9 Hz), 6.90 (1H, d, J=2.2 Hz), 7.16 (1H, d, J=8.1 Hz), 7.17 (1H, dd, J=1.7, 8.5 Hz), 7.44 (1H, t, J=8.2 Hz), 7.48 (1H, d, J=1.8 Hz), 7.49 (1H, d, J=8.6 Hz), 7.94 (1H, d, J=2.2 Hz)

FABMS (m/z): 593 [(M+Na)⁺]

Example 7

(1) 2'-(2,3-Di-O-acetyl-4,6-O-benzylidene-β-D-glucopyranosyloxy)-6'-acetoxy-3-(5-benzo[b]furanyl)propiophenone (7.20 g) is dissolved in a mixture of tetrahydrofuran (40 ml) and methanol (40 ml), and thereto are added sodium hydrogen carbonate (4.28 g) and water (0.8 ml), and the mixture is stirred at 50° C. for 6.5 hours. The sodium hydrogen carbonate is removed by filtration, and the filtrate is concentrated under reduced pressure. The residue is dissolved in ethyl acetate, and the mixture is washed with water, dried, and evaporated to remove the solvent. The residue is purified by silica gel column chromatography (solvent; chloroform/ethyl acetate) to give 2'-(2,3-di-O-acetyl-4,6-O-benzylidene-β-D-glucopyranosyloxy)-6'-hydroxy-3-(5-benzo[b]furanyl)propiophenone (5.20 g).

NMR (DMSO-$d_6$) δ: 1.98 (3H, s), 2.01 (3H, s), 2.90–3.05 (4H, m), 3.70–4.00 (3H, m), 4.25–4.35 (1H, m), 5.05 (1H, dd, J=7.9, 9.4 Hz), 5.41 (1H, t, J=9.4 Hz), 5.58 (1H, d, J=7.9 Hz), 5.63 (1H, s), 6.60 (1H, d, J=7.7 Hz), 6.68 (1H, d, J=8.1 Hz), 6.89 (1H, d, J=2.2 Hz), 7.19 (1H, dd, J=1.8, 8.6 Hz), 7.21 (1H, t, J=8.3 Hz), 7.38 (5H, s), 7.45–7.55 (2H, m), 7.94 (1H, d, J=2.2 Hz), 10.28 (1H, s)

FABMS (m/z): 639 [(M+Na)$^+$]

(2) 2'-(2,3-Di-O-acetyl-4,6-O-benzylidene-β-D-glucopyranosyloxy)-6'-hydroxy-3-(5-benzo[b]furanyl)propiophenone (1.21 g) is dissolved in acetic acid (15 ml), and thereto are added water (1.5 ml) and p-toluenesulfonic acid (43 mg), and the mixture is stirred at room temperature for 4.5 hours. To the reaction solution are added water and ethyl acetate, and the mixture is stirred. The organic layer is collected, washed with water, dried, and evaporated to remove the solvent. The residue is purified by silica gel column chromatography (solvent; chloroform/methanol) to give 2'-(2,3-di-O-acetyl-β-D-glucopyranosyloxy)-6'-hydroxy-3-(5-benzo[b]furanyl)propiophenone (915 mg).

M.p. 127°–129° C.

NMR (DMSO-$d_6$) δ: 1.92 (3H, s), 2.00 (3H, s), 2.85–3.05 (4H, m), 3.45–3.75 (4H, m), 4.75 (1H, t, J=5.4 Hz), 4.87 (1H, dd, J=8.0, 9.8 Hz), 5.09 (1H, t, J=9.7 Hz), 5.36 (1H, d, J=7.9 Hz), 5.55 (1H, d, J=5.6 Hz), 6.57 (1H, d, J=7.8 Hz), 6.68 (1H, d, J=8.1 Hz), 6.88 (1H, d, J=2.2 Hz), 7.17 (1H, d, J=9.6 Hz), 7.19 (1H, t, J=8.3 Hz), 7.48 (1H, d, J=9.3 Hz), 7.49 (1H, d, J=1.0 Hz), 7.93 (1H, d, J=2.2 Hz), 10.28 (1H, s)

FABMS (m/z): 551 [(M+Na)$^+$]

Examples 8–10

The corresponding starting compounds are treated in the same manner as in Example 7 to give the compounds as listed in Table 2.

TABLE 2

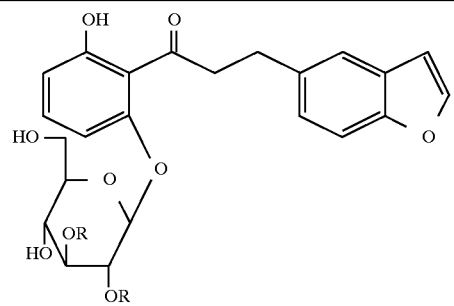

| Ex. No. | R | Physical Properties |
|---|---|---|
| 8 | CH$_3$CH$_2$OCH$_2$CO | M.p. 89–93° C. FABMS(m/z): 639[(M+Na)$^+$] |

TABLE 2-continued

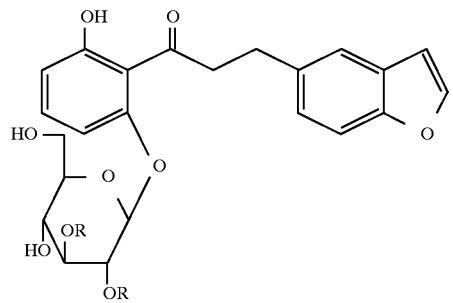

| Ex. No. | R | Physical Properties |
|---|---|---|
|   |   | NMR(DMSO-$d_6$)δ: 1.06(3H, t, J=7.0Hz), 1.12(3H, t, J=7.0Hz), 2.9–3.1(4H, m), 3.4–3.6(7H, m), 3.7–3.8(1H, m), 3.95(2H, dd, J=13.8, 16.8Hz), 4.10(2H, dd, J=9.8, 16.8Hz), 4.74(1H, t, J=5.9Hz), 4.93(1H, dd, J=8.0, 9.7Hz), 5.18(1H, t, J=9.5Hz), 5.43(1H, d, J=8.0Hz), 5.62(1H, d, J=5.5Hz), 6.58(1H, d, J=8.1Hz), 6.69(1H, d, J=8.1Hz), 6.87(1H, dd, J=1.0, 2.2Hz), 7.17(1H, dd, J=2.5, 8.3Hz), 7.19(1H, t, J=8.3Hz), 7.47(1H, d, J=9.2Hz), 7.49(1H, d, J=1.8Hz), 7.93(1H, d, J=2.2Hz), 10.28(1H, s) |
| 9 | CH$_3$OCH$_2$CO | M.p. 114–116° C. FABMS(m/z): 611[(M+Na)$^+$] NMR(DMSO-$d_6$)δ: 2.9–3.1(4H, m), 3.26(3H, s), 3.29(3H, s), 3.5–3.8(4H, m), 3.93(2H, dd, J=12.9, 16.8Hz), 4.07(2H, dd, J=8.5, 16.7Hz), 4.74(1H, t, J=5.9Hz), 4.94(1H, dd, J=7.9, 9.8Hz), 5.19(1H, t, J=9.2Hz), 5.44(1H, d, J=7.9Hz), 5.64(1H, d, J=5.5Hz), 6.58(1H, d, J=7.8Hz), 6.69(1H, d, J=8.1Hz), 6.88(1H, d, J=2.2Hz), 7.17(1H, dd, J=1.8, 8.4Hz), 7.19(1H, t, J=8.3Hz), 7.47(1H, d, J=8.3Hz), 7.49(1H, s), 7.93(1H, d, J=2.2Hz), 10.28(1H, s) |
| 10 | CH$_3$CH$_2$OCO | FABMS(m/z): 611[(M+Na)$^+$] NMR(DMSO-$d_6$)δ: 1.17(3H, t, J=7.2Hz), 1.20(3H, t, J=7.1Hz), 2.9–3.1(4H, m), 3.5–3.8(4H, m), 4.0–4.2(4H, m), 4.70(1H, dd, J=7.9, 9.8Hz), 4.74(1H, t, J=5.9Hz), 4.95(1H, t, J=9.6Hz), 5.44(1H, d, J=8.0Hz), 5.71(1H, d, J=5.9Hz), 6.58(1H, d, J=8.4Hz), 6.66(1H, d, J=7.9Hz), 6.88(1H, dd, J=1.0, 2.2Hz), 7.17(1H, dd, J=2.0, 8.8Hz), 7.19(1H, t, J=8.3Hz), 7.48(1H, d, J=9.1Hz), 7.49(1H, s), 7.93(1H, d, J=2.2Hz), 10.26(1H, s) |

Example 11

To a solution of 2'-(β-D-glucopyranosyloxy)-6'-hydroxy-3-(5-benzo[b]furanyl)propiophenone (889 mg) and ethoxyacetic acid (250 mg) in pyridine (25 ml) is added N,N-bis(2-oxo-3-oxazolidinyl)phosphinic chloride (1527 mg) under ice-cooling, and the mixture is stirred at room temperature for 19 hours. To the reaction solution are added a saturated aqueous sodium hydrogen carbonate solution and chloroform, and the mixture is stirred. The organic layer is collected, washed with water, dried, and evaporated to remove the solvent. The residue is dissolved in a mixture of methanol (10 ml) and tetrahydrofuran (10 ml), and thereto is added triethylamine (202 mg). The mixture is stirred at 50° C. for 40 minutes, and evaporated to remove the solvent. The residue is dissolved in ethyl acetate, and the mixture is washed with water, dried, and evaporated to remove the solvent. The residue is purified by silica gel column chromatography (solvent; chloroform/methanol) to give 2'-(6-O-ethoxyacetyl-β-D-glucopyranosyloxy)-6'-hydroxy-3-(5-benzo[b]furanyl)propiophenone (377 mg).

NMR (DMSO-d$_6$) δ: 1.06 (3H, t, J=7.0 Hz), 2.99 (2H, t, J=7.4 Hz), 3.1–3.3 (5H, m), 3.41 (2H, q, J=7.0 Hz), 3.6–3.7 (1H, m), 3.96 (1H, d, J=16.6 Hz), 4.03 (1H, d, J=16.6 Hz), 4.1–4.2 (1H, m), 4.36 (1H, dd, J=1.8, 11.7 Hz), 4.98 (1H, d, J=7.3 Hz), 5.22 (1H, d, J=4.5 Hz), 5.31 (1H, d, J=5.5 Hz), 5.34 (1H, d, J=5.2 Hz), 6.56 (1H, d, J=8.1 Hz), 6.64 (1H, d, J=8.1 Hz), 6.87 (1H, dd, J=1.0, 2.2 Hz), 7.20 (1H, dd, J=1.8, 8.1 Hz), 7.23 (1H, t, J=8.3 Hz), 7.46 (1H, d, J=8.4 Hz), 7.51 (1H, d, J=1.4 Hz), 7.93 (1H, d, J=2.2 Hz), 10.87 (1H, s)

FABMS (m/z): 553 [(M+Na)$^+$]

Examples 12–15

The corresponding starting compounds are treated in the same manner as in Example 11 to give the compounds as listed in Table 3.

TABLE 3

| Ex. No. | R | Physical Properties |
|---|---|---|
| 12 | CH$_3$OCH$_2$CO | FABMS(m/z): 539[(M+Na)$^+$]<br>NMR(DMSO-d$_6$)δ: 2.99(2H, t, J=7.1Hz), 3.24(3H, s), 3.15–3.40(5H, m), 3.60–3.70(1H, m), 3.94(1H, d, J=16.6Hz), 4.00(1H, d, J=16.6Hz), 4.16(1H, dd, J=6.8, 11.9Hz), 4.37(1H, dd, J=1.8, 11.8Hz), 4.98(1H, d, J=7.4Hz), 5.23(1H, d, J=4.8Hz), 5.33(1H, d, J=4.8Hz), 5.36(1H, d, J=5.3Hz), 6.56(1H, d, J=8.1Hz), 6.64(1H, d, J=8.1Hz), 6.88(1H, d, J=2.7Hz), 7.20(1H, dd, J=1.8, 8.2Hz), 7.24(1H, d, J=8.3Hz), 7.46(1H, d, J=8.4Hz), 7.51(1H, d, J=1.4Hz), 7.93(1H, d, J=2.2Hz), 10.86(1H, s) |
| 13 | CH$_3$CO | FABMS(m/z): 509[(M+Na)$^+$]<br>NMR(DMSO-d$_6$)δ: 1.95(3H, s), 2.99(2H, t, J=7.4Hz), 3.2–3.4(5H, m), 3.5–3.7(1H, m), 4.07(1H, dd, J=6.6, 11.8Hz), 4.28(1H, dd, J=2.0, 11.9Hz), 4.97(1H, d, J=7.5Hz), 5.20(1H, d, J=4.6Hz), 5.29(1H, d, J=5.5Hz), 5.34(1H, d, J=5.2Hz), 6.56(1H, d, J=8.1Hz), 6.65(1H, d, J=8.1Hz), 6.87(1H, d, J=2.2Hz), 7.20(1H, dd, J=1.8, 8.3Hz), 7.24(1H, t, J=8.3Hz), 7.46(1H, d, J=8.4Hz), 7.51(1H, d, J=1.4Hz), 7.93(1H, d, J=2.2Hz), 10.86(1H, s) |
| 14 | C$_6$H$_5$CO | FABMS(m/z): 571[(M+Na)$^+$]<br>NMR(DMSO-d$_6$)δ: 2.37(2H, t, J=7.3Hz), 3.20–3.40(5H, m), 3.75–3.85(1H, m), 4.28(1H, dd, J=7.5, 11.8Hz), 4.60(1H, dd, J=1.8, 10.7Hz), 5.02(1H, d, J=7.4Hz), 5.28(1H, d, J=4.0Hz), 5.40(1H, d, J=5.2Hz), 5.42(1H, d, J=5.3Hz), 6.53(1H, d, J=8.1Hz), 6.68(1H, d, J=8.1Hz), 6.86(1H, dd, J=1.0, 2.2Hz), 7.06(1H, t, J=8.3Hz), 7.17(1H, dd, J=1.8, 8.5Hz), 7.44(1H, d, J=8.4Hz), 7.49(1H, d, J=1.4Hz), 7.52(2H, t, J=7.8Hz), 7.67(1H, t, J=7.5Hz), 7.93(1H, d, J=2.2Hz), 7.95(2H, d, J=7.0Hz), 10.28(1H, s) |
| 15 | CH$_3$(CH$_2$)$_{14}$CO | FABMS(m/z): 705[(M+Na)$^+$]<br>NMR(DMSO-d$_6$)δ: 0.85(3H, t, J=7.0Hz), 1.10–1.30(24H, m), 1.40–1.50(2H, m), 2.20(2H, t, J=7.7Hz), 2.99(2H, t, J=7.3Hz), 3.25–3.35(5H, m), 3.55–3.65(1H, m), 4.06(1H, dd, J=6.8, 11.9Hz), 4.31(1H, dd, J=1.6, 11.8Hz), 4.97(1H, d, J=7.4Hz), 5.24(1H, d, J=4.8Hz), 5.31(1H, d, J=5.5Hz), 5.37(1H, d, J=5.2Hz), 6.56(1H, d, J=8.1Hz), 6.64(1H, d, J=8.1Hz), 6.87(1H, dd, J=1.0, 2.2Hz), 7.20(1H, dd, J=1.8, 8.5Hz), 7.22(1H, t, J=8.4Hz), 7.45(1H, d, J=8.5Hz), 7.51(1H, d, J=1.3Hz), 7.93(1H, d, J=2.2Hz), 10.92(1H, s) |

Example 16

2'-[2,3,6-Tri-O-acetyl-4-O-(2,3,4,6-tetra-O-acetyl-(α-D-glucopyranosyl)-β-D-glucopyranosyloxy]-6'-hydroxyacetophenone (1541 mg) and benzo[b]furan-5-carbaldehyde (350 mg) are treated in the same manner as in Example 1 or 2 to give 2'-[4-O-(α-D-glucopyranosyl)-β-D-glucopyranosyloxy]-6'-hydroxy-3-(5-benzo[b]furanyl)propiophenone (415 mg).

NMR (DMSO-d$_6$) δ: 3.00 (2H, t, J=7.4 Hz), 3.0–3.8 (14H, m), 4.4–4.6 (2H, broad), 4.90 (2H, broad), 4.99 (1H, d, J=7.7 Hz), 5.06 (1H, d, J=3.7 Hz), 5.38 (1H, d, J=5.4 Hz), 5.47 (1H, broad), 5.60 (1H, broad), 6.56 (1H, dd, J=0.7, 8.4 Hz), 6.69 (1H, d, J=7.9 Hz), 6.88 (1H, dd, J=1.0, 2.2 Hz), 7.21 (1H, dd, J=1.8, 8.5 Hz), 7.24 (1H, t, J=8.3 Hz), 7.46 (1H, d, J=8.5 Hz), 7.53 (1H, d, J=1.2 Hz), 7.92 (1H, d, J=2.2 Hz), 10.95 (1H, s)

FABMS (m/z): 629 [(M+Na)$^+$]

Example 17

2'-[2,3,6-Tri-O-acetyl-4-O-(2,3,4,6-tetra-O-acetyl-α-D-glucopyranosyl)-β-D-glucopyranosyloxy]-6'-hydroxyacetophenone (1541 mg) and benzo[b]thiophene-5-carbaldehyde (389 mg) are treated in the same manner as in Example 1 to give 2'-[4-O-(α-D-glucopyranosyl)-β-D-glucopyranosyloxy]-6'-hydroxy-3-(5-benzo[b]thienyl)propiophenone (645 mg).

NMR (DMSO-d$_6$) δ: 3.03 (2H, t, J=7.6 Hz), 3.0–3.8 (14H, m), 4.51 (1H, t, J=5.5 Hz), 4.57 (1H, t, J=5.6 Hz), 4.88 (1H, d, J=4.9 Hz), 4.91 (1H, d, J=5.6 Hz), 5.00 (1H, d, J=7.7 Hz), 5.06 (1H, d, J=3.8 Hz), 5.40 (1H, d, J=5.7 Hz), 5.47 (1H, d, J=6.0 Hz), 5.61 (1H, d, J=3.3 Hz), 6.56 (1H, d, J=8.4 Hz), 6.69 (1H, d, J=7.9 Hz), 7.25 (1H, t, J=8.3 Hz), 7.29 (1H, dd, J=1.6, 8.7 Hz), 7.39 (1H, d, J=5.5 Hz), 7.70 (1H, d, J=5.4 Hz), 7.77 (1H, d, J=1.6 Hz), 7.87 (1H, d, J=8.2 Hz), 10.97 (1H, s)

FABMS (m/z): 645 [(M+Na)$^+$]

Example 18

2'-(2,3,4,6-Tetra-O-acetyl-α-D-glucopyranosyloxy)-6'-hydroxyacetophenone (5 g) and benzo[b]furan-5-carbaldehyde (1.81 g) are (i) treated in the same manner as in Example 1 to give crude 2'-(β-D-glucopyranosyloxy)-6'-hydroxy-3-(5-benzo[b]furanyl)acrylophenone, which is dissolved in a mixture of ethanol (50 ml) and a 10% aqueous potassium hydroxide solution (10 ml). The mixture is subjected to catalytic hydrogenation by using as a catalyst platinum oxide (120 mg) under atmospheric pressure. The catalyst is removed by filtration, and the filtrate is neutralized with a 10% hydrochloric acid under ice-cooling, and concentrated under reduced pressure. To the residue is added ethyl acetate, and the mixture is stirred, and the organic layer is collected; (ii) treated in the same manner as in Example 1 to give crude 2'-(β-D-glucopyranosyloxy)-6'-hydroxy-3-(5-benzo[b]furanyl)acrylophenone, which is dissolved in a mixture of ethanol (50 ml) and a 10% aqueous potassium hydroxide solution (10 ml). To the solution is added 4-N,N-diemethylaminopyridine (2.5 g) and the mixture is subjected to catalytic hydrogenation by using as a catalyst 10% palladium-carbon (1.1 g) under atmospheric pressure. The catalyst is removed by filtration, and the filtrate is neutralized with a 10% hydrochloric acid under ice-cooling, and concentrated under reduced pressure. To the residue is added ethyl acetate, and the mixture is stirred, and the organic layer is collected; or (iii) treated in the same manner as in Example 2, and the organic layer is collected.

The organic layer thus obtained is washed with water, dried, and evaporated to remove the solvent. The resulting residue is purified by silica gel column chromatography to give 2'-(β-D-glucopyranosyloxy)-6'-hydroxy-3-(5-benzo[b]furanyl)propiophenone (3.4 g). The physical properties of the product are the same as those of the compound of Example 1.

Example 19

The corresponding starting compounds are treated in the same manner as in Example 11 to give 2'-(6-O-methoxycarbonyl-β-D-glucopyranosyloxy)-6'-hydroxy-3-(5-benzo[b]furanyl)propiophenone.

NMR (DMSO-$d_6$) δ: 2.99 (2H, t, J=7.5 Hz), 3.1–3.4 (5H, m), 3.63 (1H, m), 3.64 (3H, s), 4.15 (1H, dd, J=6.4, 11.6 Hz), 4.36 (1H, dd, J=2.0, 11.6 Hz), 4.98 (1H, d, J=7.6 Hz), 5.21 (1H, d, J=4.9 Hz), 5.34 (1H, d, J=5.4 Hz), 5.35 (1H, d, J=5.4 Hz), 6.56 (1H, d, J=8.1 Hz), 6.64 (1H, d, J=8.1 Hz), 6.87 (1H, dd, J=1.0, 2.2 Hz), 7.20 (1H, dd, J=1.8, 8.5 Hz), 7.22 (1H, t, J=8.3 Hz), 7.46 (1H, d, J=8.4 Hz), 7.51 (1H, d, J=1.5 Hz), 7.92 (1H, d, J=2.2 Hz), 10.88 (1H, s)

FABMS (m/z): 525 [(M+Na)$^+$]

Reference Example 1

A mixture of 2',6'-dihydroxyacetophenone (1.065 g), cadmium carbonate (4.83 g) and toluene (100 ml) is refluxed during which the solvent is removed by a Dien-Stark trap. After 30 ml of the solvent is removed, to the reaction mixture is added 2,3,6-tri-O-acetyl-4-O-(2,3,4,6-tetra-O-acetyl-α-D-glucopyranosyl)-β-D-glucopyranosyl bromide (11.42 g), and the mixture is refluxed for 17 hours. After cooling, the insoluble materials are removed by filtration, and the filtrate is concentrated. The residue is purified by silica gel column chromatography to give 2'-O-[2,3,6-tri-O-acetyl-4-O-(2,3,4,6-tetra-O-acetyl-α-D-glucopyranosyl)-β-D-glucopyranosyl]-6'-hydroxyacetophenone (4.30 g).

IR (nujol) cm$^{-1}$: 1750, 1630

NMR (CDCl$_3$) δ: 2.01 (3H, s), 2.03 (6H, s), 2.04 (3H, s), 2.06 (3H, s), 2.08 (3H, s), 2.10 (3H, s), 2.59 (3H, s), 3.8–4.35 (6H, m), 4.46 (1H, dd, J=2.9, 12.2 Hz), 4.87 (1H, dd, J=4.2, 10.5 Hz), 5.06 (1H, t, J=9.8 Hz), 5.21 (1H, d, J=7.3 Hz), 5.32 (1H, d, J=2.5 Hz), 5.35–5.47 (3H, m), 6.49 (1H, d, J=8.3 Hz), 6.71 (1H, d, J=8.3 Hz), 7.36 (1H, t, J=8.3 Hz), 12.96 (1H, s)

FABMS (m/z): 793 [(M+Na)$^+$]

[Effects of the Invention]

The desired propiophenone derivatives [I] of the present invention and pharmaceutically acceptable salts thereof have excellent hypoglycemic activity based on the inhibitory activity of renal glucose reabsorption thereof, by which they are useful in the treatment or prophylaxis of diabetes. For example, when administered orally to rats, the present compounds increase the amount of urine glucose 11 to 100 times as much as phlorizin does.

In addition, the desired propiophenone derivatives [I] of the present invention and pharmaceutically acceptable salts thereof have low toxicity. For example, when 2'-(p-D-glucopyranosyloxy)-6'-hydroxy-3-(5-benzo[b]furanyl)propiophenone or 2'-(2,3-di-O-acetyl-β-D-glucopyranosyloxy)-6'-hydroxy-3-(5-benzo[b]furanyl)propiophenone was orally administered once to rats at a dose of 3000 mg/kg, no rat died. Besides, the aglycone of the desired propiophenone compound [I], a hydrolysate thereof, shows extremely weak inhibitory activity of facilitated diffusion-type glucose transporter.

Thus, the desired compound [I] of the present invention can treat hyperglycemia, by which the self-exacerbating cycle of glucose-toxicity is interrupted, so that the propiophenone derivatives [I] and pharmaceutically acceptable salts thereof are useful in the prophylaxis or treatment of diabetes such as insulin-dependent diabetes (I-type diabetes), insulin-independent diabetes (II-type diabetes).

What is claimed is:

1. A propiophenone derivative of the formula [I]:

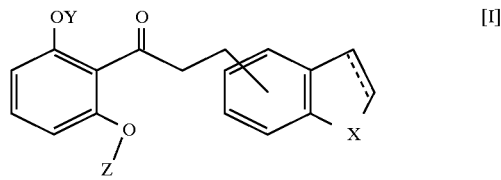

wherein X is an oxygen atom, a sulfur atom or a methylene group, OY is a protected or unprotected hydroxy group, Z is a β-D-glucopyranosyl group or 4-O-(α-D-glucopyranosyl)-β-D-glucopyranosyl group wherein one or more hydroxy groups of these groups may optionally be acylated, and the dotted line means the presence or absence of a double bond, or a pharmaceutically acceptable salt thereof.

2. The compound according to claim 1, wherein Z is a β-D-glucopyranosyl group or 4-O-(α-D-glucopyranosyl)-β-D-glucopyranosyl group wherein one or more hydroxy groups of these groups may optionally be acylated by a group selected from the group consisting of a $C_{2-20}$ alkanoyl group, a lower alkoxy-lower alkanoyl group, a lower alkoxycarbonyl group and a benzoyl group.

3. The compound according to claim 1, wherein OY is a lower alkanoyloxy group or hydroxy group, Z is a β-D-glucopyranosyl group wherein the 2- and the 3-hydroxy groups or the 6-hydroxy group may optionally be acylated by a group selected from the group consisting of a $C_{2-20}$ alkanoyl group, a lower alkoxy-lower alkanoyl group, a lower alkoxycarbonyl group and a benzoyl group, and the dotted line means the presence of a double bond.

4. The compound according to claim 1, wherein X is an oxygen atom or a sulfur atom, OY is a hydroxy group, Z is a β-D-glucopyranosyl group wherein the 2- and the 3-hydroxy groups or the 6-hydroxy group may optionally be acylated by a group selected from the group consisting of a $C_{2-20}$ alkanoyl group, a lower alkoxy-lower alkanoyl group, a lower alkoxycarbonyl group and a benzoyl group, and the dotted line means the presence of a double bond.

5. The compound according to claim 1, wherein X is an oxygen atom or a sulfur atom, OY is a hydroxy group, Z is a β-D-glucopyranosyl group or a 4-O-(α-D-glucopyranosyl)-β-D-glucopyranosyl group.

6. The compound according to claim 3, wherein X is an oxygen atom, OY is a lower alkanoyloxy group or a hydroxy group, Z is a 2,3-di-O-(lower alkanoyl)-β-D-glucopyranosyl group, a 2,3-di-O-(lower alkoxy-lower alkanoyl)-β-D-glucopyranosyl group, a 6-O-($C_{2-20}$-alkanoyl)-β-D-glucopyranosyl group, a 6-O-(lower alkoxy-lower alkanoyl)-β-D-glucopyranosyl group or a 6-O-benzoyl-β-D-glucopyranosyl group.

7. The compound according to claim 6, wherein X is an oxygen atom, OY is a lower alkanoyloxy group or a hydroxy group, Z is a 2,3-di-O-(lower alkanoyl)-β-D-glucopyranosyl group.

8. 2'-[2,3-di-O-(Lower alkanoyl)-β-D-glucopyranosyloxy]-6'-hydroxy-3-(5-benzo[b]furanyl)propiophenone or 2'-[2,3-di-O-(lower alkanoyl)-β-D-glucopyranosyloxy]-6'-(lower alkanoyloxy)-3-(5-benzo[b]furanyl)propiophenone.

9. A pharmaceutical composition which comprises a therapeutically effective amount of the compound set forth in any one of claims 1–8 in admixture with a pharmaceutically acceptable carrier or diluent.

10. A method of increasing the amount of glucose in urine in a patient in need thereof, which comprises administering to said patient a therapeutically effective amount of a compound of the formula (1) as set forth in any one of claims 1–8.

11. A propiophenone derivative of the formula:

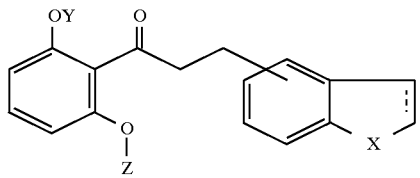

wherein X is an oxygen atom, OY is a lower alkanoyloxy group or a hydroxy group, Z is a β-D-glucopyranosyl group, and the dotted line means the presence of a double bond, or a pharmaceutically acceptable salt thereof.

12. 2'-(β-D-glucopyranosyloxy)-6'-hydroxy-3-(5-benzo(b)furanyl)-propiophenone or a pharmaceutically acceptable salt thereof.

13. A propiophenone derivative of the formula:

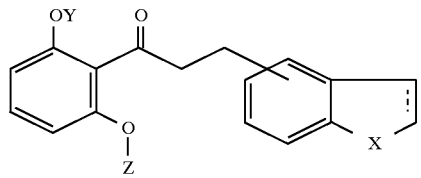

wherein X is an oxygen atom or a sulfur atom, OY is a hydroxy group, Z is a 6-O-(lower alkoxycarbonyl)-β-D-glucopyranosyl group, and the dotted line means the presence or absence of a double bond, or a pharmaceutically acceptable salt thereof.

14. A propiophenone derivative of the formula:

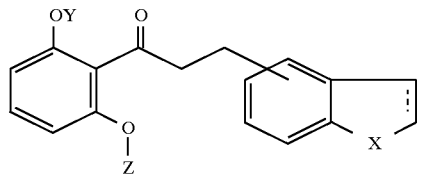

wherein X is an oxygen atom, OY is a lower alkanoyloxy group or a hydroxy group, Z is a 6-O-(lower alkoxycarbonyl)-β-D-glucopyranosyl group, and the dotted line means the presence of a double bond, or a pharmaceutically acceptable salt thereof.

15. 2'-(6-O-(lower alkoxycarbonyl)-β-D-glucopyranosyloxy)-6'-hydroxy-3-(5-benzo(b)furanyl)propiophenone or a pharmaceutically acceptable salt thereof.

16. 2'-(6-O-methoxycarbonyl-β-D-glucopyranosyloxy)-6'-hydroxy-3-(5-benzo(b)furanyl)propiophenone or a pharmaceutically acceptable salt thereof.

17. A method of normalizing blood glucose concentration comprising increasing the amount of glucose in urine with the method of claim 10.

18. A method of treating diabetes comprising increasing the amount of glucose in urine with the method of claim 10.

* * * * *